United States Patent [19]
Wei et al.

[11] Patent Number: 5,583,108
[45] Date of Patent: Dec. 10, 1996

[54] VASONATRIN PEPTIDE AND ANALOGS THEREOF

[75] Inventors: Chi-Ming Wei; John C. Burnett, both of Rochester, Minn.

[73] Assignee: Mayo Foundation for Medical Education and Research, Rochester, Minn.

[21] Appl. No.: 297,330

[22] Filed: Aug. 29, 1994

Related U.S. Application Data

[63] Continuation of Ser. No. 25,935, Mar. 3, 1993, abandoned.
[51] Int. Cl.$^6$ .................... A61K 38/16; C07K 14/00; C07K 14/58
[52] U.S. Cl. ................ 514/12; 514/13; 530/324; 530/325; 530/326; 530/317
[58] Field of Search .................. 514/12, 13; 530/324, 530/325, 326, 317

[56] References Cited

U.S. PATENT DOCUMENTS

| | | | |
|---|---|---|---|
| 4,757,048 | 7/1988 | Lewicki et al. | 514/11 |
| 4,804,650 | 2/1989 | Lewicki et al. | 514/15 |
| 4,935,492 | 6/1990 | Lewicki et al. | 530/324 |
| 5,047,397 | 9/1991 | Scarborough | 514/12 |
| 5,114,923 | 5/1992 | Seilhamer et al. | 514/12 |
| 5,202,239 | 4/1993 | Tarnowski et al. | 435/69.7 |
| 5,212,286 | 5/1993 | Lewicki et al. | 530/324 |
| 5,434,133 | 7/1995 | Tanaka et al. | 514/12 |

FOREIGN PATENT DOCUMENTS 0497368 8/1992 European Pat. Off. .

OTHER PUBLICATIONS

*FEBS*, vol. 309, No. 2, Sep. 1992, pp. 185–189, Y. Shimekake et al., "The Role of the C–Terminal Region of Rat Brain Natriuretic Peptide in Receptor Selectivity".

*Biochem. Biophs. Res. Commun.*, vol. 183, No. 3, 31 Mar. 1992, pp. 964–969, M. Furuya et al., "Structural Requirements of C–Type Natriuretic Peptide for Elevation of Cyclic GMP in Cultured Vascular Smooth Muscle Cells".

B. M. Brenner et al., "Diverse Biological Actions of Atrial Natriuretic Peptide", *Physiol. Rev.*, 70, 665–699 (1990).

Burnett et al., "Effects of Synthetic Atrial Natriuretic Factor on Renal Function and Renin Release", *Am J. Physiol.*, 247, F863–866 (1984).

Burnett et al., "Atrial Natriuretic Peptide Elevation in Congestive Heart Failure in the Human", *Science*, 231, 1145–1147 (1986).

Carpino et al., "The 9–Fluorenylmethoxycarbonyl Amino–Protecting Group", *J. Org. Chem.*, 37, 3404–3409 (1972).

A. J. de Bold et al., "A Rapid and Potent Natriuretic Response to Intravenous Injection of Atrial Myocardial Extract in Rats", *Life Sci.*, 28, 89–94 (1981).

T. G. Flynn et al., "The Amino Acid Sequence of an Atrial Peptide with Potent Diuretic and Natriuretic Properties", *Biochem. Biophys. Res. Commun.*, 117, 859–865 (1981).

Hughes et al., "The Effect of Atrial Natriuretic Peptide on Human Blood Vessels", *J. Hypertension*, 5, S51–S53 (1987).

Y. Kambayashi et al., "Isolation and Sequence Determination of Human Brain Natriuretic Peptide in Human Atrium", *FEBS Lett.*, 259, 341–345 (1990).

K. J. Koller et al., "Molecular Biology of the Natriuretic Peptides and Their Receptors", *Circulation*, 86, 1081–1088 (1992).

(List continued on next page.)

*Primary Examiner*—Christina Y. Chan
*Assistant Examiner*—T. D. Wessendorf
*Attorney, Agent, or Firm*—Schwegman, Lundberg, Woessner & Kluth, P.A.

[57] ABSTRACT

Synthetic analogs of C-type natriuretic peptide are provided, together with methods for their production and use as natriuretics, diuretics, and/or vasodilators, or as intermediates for or modulators of such useful compounds or of native natriuretic peptides.

2 Claims, 1 Drawing Sheet

OTHER PUBLICATIONS

K. J. Koller et al., "Selective Activation of the B Natriuretic Peptide Receptor by C–Type Natriuretic Peptide (CNP)".

Meinhofer and Chang, "Solid–Phase Peptide Synthesis Using Mild Base Cleavage of $N^{alpha}$–Fluorenylmethyloxycarbonylamino Acids, Exemplified by a Synthesis of Dihydrosomatostatin", *Int. J. Pept. Pro. Res.*, 11, 246–249 (1978).

Merrifield, "Solid Phase Peptide Synthesis. I. The Synthesis of a Tetrapeptide", *J. Am. Chem. Soc.*, 85, 2149–2154 (1963).

A. J. Stingo et al., "Cardiovascular and Renal Actions of C–Type Natriuretic Peptide", *Am. J. Physiol.*, 262, H308–H312 (1992).

T. Sudoh et al., "C–Type Natriuretic Peptide (CNP): A New Member of Natriuretic Peptide Family Identified in Porcine Brain", *Biochem. Biophys. Res. Commun.*, 168, 863–870 (1990).

T. Sudoh et al., "A New Natriuretic Peptide in Porcine Brain", *Nature*, 332, 78–81 (1988).

Y. Tawaragi et al., "Gene and Precursor Structures of Human C–Type Natriuretic Peptide", *Biochem. Biophys. Res. Commun.*, 175, 645–651 (1991).

C. M. Wei et al., "Action of C–type Natriuretic Peptide in Isolated Canine Arteries and Veins", *Am. J. Physiol.*, 264, H71–H73 (1993).

VASONATRIN PEPTIDE AND ANALOGS THEREOF

BACKGROUND OF THE INVENTION

This invention was made with the support of the U.S. Government under National Heart, Lung and Blood Institute (NHLBI) Grants HL-36634 and HL07111. The U.S. Government has certain rights in the invention.

This is a continuation of application Ser. No. 08/025,935 filed Mar. 3, 1993, now abandoned.

Atrial natriuretic peptide (ANP) is the first described peptide in a family of hormones known to have important roles in the regulation of body fluid homeostasis. See, B. M. Brenner et al., *Physiol. Rev.*, 70, 665 (1990). The description of the potent diuretic and natriuretic properties of atrial extracts by A. J. de Bola et al., *Life Sci.*, 28, 89 (1981) was the first evidence that the heart could be an endocrine organ. The subsequent isolation and characterization of this activity by T. G. Flynn et al., *Biochem. Biophys. Res. Commun.*, 117, 859 (1981) and other groups characterized ANP as the first secreted cardiac hormone. It is secreted by atrial myocytes in response to increased intravascular volume. Once it is in the circulation, its effects are primarily on the kidney, vascular tissue, and adrenal gland, in which its actions lead to the excretion of sodium (natriuresis) and water (diuresis) by the kidneys and a decrease in intravascular volume and blood pressure. (S. A. Atlas et al., in *Atrial Hormones and Other Natriuretic Factors*, P. J. Mulrow et al, ed., Am. Physiol. Soc., Bethesday, Md. (1987) at pages 53–76.)

Figure 1:
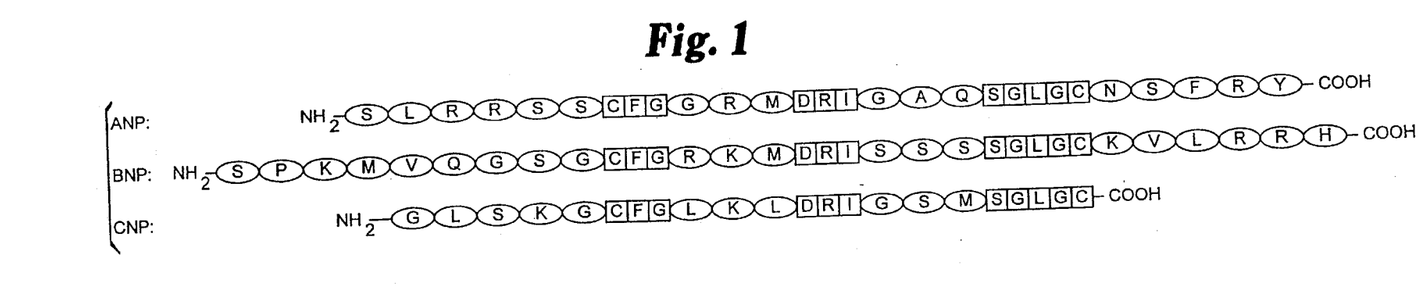
FIG. 1 is a diagrammatic comparison of the mature human atrial (SEQ ID NO: 1) (ANP), brain (BNP) (SEQ ID NO: 2) and C-type (CNP) (SEQ ID NO: 3) natriuretic peptides. Conserved residues of ANP, BNP, and CNP are represented by darkened boxes. The line between the two cysteines in each peptide indicates a disulfide bridge. From *Circulation*, 86, 1082 (1992)). Single-letter and three-letter abbreviations for the amino acid residues are A, alanine (Ala); R, arginine (Arg); N, asparagine (Asn); D, aspartic acid (Asp); C, cysteine (Cys); Q, glutamine (Gln); E, glutamic acid (Glu); G, glycine (Gly); H, histidine (His); I, isoleucine (Ile); L, leucine (Leu); K, lysine (Lys); F, phenylalanine (Phe); M, methionine (Met); P, proline (Pro); S, serine (Ser); T, threonine (Thr); W, tryptophan (Trp); Y, tyrosine (Tyr); V, valine (Val).

More recently, Matsuo and his coworkers have isolated two new natriuretic peptides. Brain natriuretic peptide (BNP) and C-type natriuretic peptide (CNP) were both isolated from porcine brain extracts on the basis of their potent relaxant effects on chick rectum. (See T. Sudeh et al., *Nature*, 332, 78 (1988); *Biochem. Biophys. Res. Commun.*, 168, 863 (1990)). Like ANP, these hormones are synthesized from large precursor proteins, and the mature, active peptides have a 17-amino-acid loop formed by an intramolecular disulfide linkage. In the human peptides (FIG. 1), eleven of these amino acids are identical in ANP, BNP, and CNP, whereas the N- and C-terminal tails vary in both length and composition. See, Y. Kambayashi et al., *FEBS Lett.*, 259, 341 (1990); Y. Tawaragi et al., *Biochem. Biophys. Res. Commun.*, 175, 645 (1991). CNP has no C-terminal tail, and studies of the structure of the gene for CNP demonstrated that translation is terminated by a stop codon immediately after the final cysteine codon in the mRNA.

Among species, the amino acid sequence of both ANP and CNP are highly conserved, whereas the structure of BNP varies greatly. For example, the mature 28-amino-acid human and porcine ANPs are identical, and there is only one substitution in the rat peptide. This existence of this structural variation, coupled with the presence of at least three types of receptors specific for the natriuretic peptides, suggests that the physiological control of body fluid homeostasis is complex. ANP and CNP both decrease cardiac preload. However, unlike ANP, CNP is not natriuretic. See, A. J. Stingo et al., *Am. J. Physiol.*, 262, H308 (1992). The diverse actions of ANP, BNP and CNP on both the cardiovascular system and the kidney as well as their roles in pathophysiological states such as heart failure, hypertension, and renal disease have made the native peptides and their analog molecules of great interest to both clinical and basic scientists. See, for example, J. A. Lewicki et al. (U.S. Pat. Nos. 5,114,923, 4,804,650 and U.S. Pat. No. 4,757,048), L. K. Johnson et al. (U.S. Pat. No. 5,047,397) and L. K. Johnson et al. (U.S. Pat. No. 4,935,492). Therefore, a continuing need exists to identify and characterize bioactive peptides belonging, or related to, this class of materials. Such peptides may be useful both to elucidate the mechanism of action of these compounds, as well as to provide new pharmaceutical agents with useful profiles of bioactivity.

SUMMARY OF THE INVENTION

The present invention provides a peptide compound having natriuretic, diuretic and/or vasodilator activity in mammals, which has the formula (I):

$$X_1—A_y—X_2—A_1—A_2—A_3—A_4—A_5—X_3—A_z—X_y \qquad (I)$$

wherein $A_1$ is Lys, Arg, Orn, Ala, Thr, Asn or Gln; $A_2$ is Ile, Met, Val or Leu; $A_3$ is Glu or Asp; $A_4$ is Lys, Arg, Orn, Ala, Thr, Asn or Gln; $A_5$ is Val, Leu or Ileu; $X_1$ is a peptide of from 1–125 amino acid residues, preferably 1–5 amino acid residues comprising Gly at the carboxyl terminus, and preferably Gly at the N-terminus, with the remainder being individually selected from the group consisting of Leu, Ser and Lys. Most preferably, $X_1$ is (H)-Gly-Leu-Ser-Lys-Gly (SEQ ID NO; 5), or an N-terminal deleted form such as (H)Leu-Ser-Lys-Gly (SEQ ID NO: 5), (H)Ser-Lys-Gly, (H)Lys-Gly or (H)Gly; $A_y$ and $A_z$ are amino acid residues which together form a bridging bond, wherein said bond is selected from the group consisting of disulfide, methylene, sulfide/methylene, amide and ester; preferably, disulfide; $X_2$ is a peptide of 1–10 amino acid residues, preferably of about 1–3 residues, individually selected from the group consisting of Phe, Trp, Val, Leu, Ile, Gly, Ser and Cys; $X_3$ is a peptide of 1–10 amino acid residues, preferably about 1–7 residues and $X_y$ is a peptide of about 1–5 residues selected from the group consisting of R-Asn-, R-Ser-Asn, R-Phe-Ser-Asn, R-Arg-Phe-Ser-Asn-(SEQ ID NO: 7) and R-Tyr-Arg-Phe-Ser-Asn-(SEQ ID NO: 8) wherein R is OH, $NH_2$, $NHR^3$ or $NR^3R^4$, wherein $R^3$ and $R^4$ are independently $(C_1-C_4)$alkyl, $(C_3-C_5)$cycloalkyl, phenyl or benzyl. Preferably, $X_3$ is a heptapeptide comprising peptidyl residues individually selected from the group consisting of Gly, Ser, Met and Leu. Preferably, when $A_2$ is Ile, $A_1$ is not Arg, and when $A_2$ is Arg, $A_2$ is not Ile.

Preferably, the total ring size is equivalent to that obtained by disulfide bridge formation between cysteine residues separated by 7–15 amino acid (peptidyl) residues. Optionally, one or more of the amide linkages between adjacent amino acid residues can be replaced by a linkage such as $—CH_2—NH—$, $—CH_2—S—$, $—CH_2CH_2—$, $—CH=CH—$, $—COCH_2—$, $—CH(OH)CH_2—$ or $—CH_2SO—$. $X_1$ can also be an amino acid protecting group such as fluorenylmethyloxycarbonyl, benzyloxycarbonyl, (2-(2',6'-methoxynaphthyl)propionyl, diphenylpropionyl, cyclohexylacetyl, 3-indolepropionyl, 2-naphthoxy and the like. Other such groups are disclosed in U.S. Pat. No. 4,935,492.

In the peptides of the invention, the L-form of any amino acid residue having an optical isomer is intended unless otherwise indicated. In some cases, $A_2$ and/or $A_5$ can be replaced by the D-forms. Bioactive peptides of formula (I) which do not comprise the disulfide bond are also within the scope of the invention.

Figure 2:
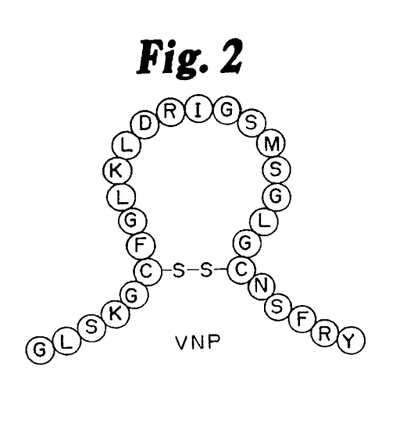
FIG. 2 depicts the structure of vasonatrin peptide (VNP) (SEQ ID NO: 4). The amino terminus of the peptide is at the left-hand end of the peptide, while the carboxyl terminus is at the right-hand end.

In a preferred embodiment, the present invention provides a peptide having natriuretic, diuretic and/or vasodilator activity in mammals, of the formula (II):

(SEQ ID NO: 9), wherein A' is Lys or Arg, A" is Leu, Ile or Met and $R^2$ is R-Asn-, R-Ser-Asn-, R-Phe-Ser-Asn-, R-Arg-Phe-Ser-Asn-(SEQ ID NO: 7) and R-Tyr-Arg-Phe-Ser-Asn-(SEQ ID NO: 8); wherein R is OH, $NH_2$, $NHR^3$ or $NR^3R^4$ wherein $R^3$ and $R^4$ are independently phenyl or ($C_1$–$C_4$)alkyl; and wherein the bracket connecting the two cysteinyl moieties of formula (I) indicates that they are connected by a disulfide bond as depicted on FIG. 2. Preferably, $R^2$ is R-Tyr-Arg-Phe-Ser-Asn-(SEQ ID NO: 8), and most preferably, R is OH, i.e., H in formula (I) represents the amino terminus of the peptide and (OH) represents the carboxyl terminus of the peptide. Preferably, A' is Lys (K) and A" is Leu (L). Thus, using single letter amino acid code, this preferred peptide, or "VNP", can be represented as:

(SEQ ID NO: 4), wherein the sequence is read conventionally, from the left, amino terminus to the right, carboxy terminus. The bracket represents a disulfide bond between the cysteinyl residues.

VNP is a more potent, endothelium independent, vasorelaxing peptide in both arteries and veins than ANP or CNP. VNP also has potent natriuretic effects in vivo. Thus, the present invention also provides a composition useful as a natriuretic, diuretic and/or vasodilator comprising a therapeutically effective amount of the present peptide in combination with a pharmaceutically acceptable carrier, and a method for _inducing natriuresis, diuresis or vasodilation in a mammal, preferably a human, comprising administering to said mammal a pharmaceutically effective amount of said composition. The present compositions can also be employed to modify the renin-angiotensis-aldosterone system.

Thus, the present peptides may be useful, either singly or in combination, to treat (ameliorate or prevent) a number of pathological conditions, including acute or chronic kidney failure, hypertension, congestive heart failure, cirrhosis of the liver, nephrotic syndrome, and other "edematous states".

DETAILED DESCRIPTION OF THE INVENTION

1. Synthesis

Peptides of this invention can be synthesized by the solid phase peptide synthesis (or Merrifield) method. This established and widely used method, including the experimental procedures, is described in the following references: Stewart et al., *Solid Phase Peptide Synthesis*, W. H. Freeman Co., San Francisco (1969); Merrfield, *J. Am. Chem. Soc.*, 85, 2149 (1963); Meienhofer in "Hormonal Proteins and Peptides," ed.; C. H. Li, Vol. 2 (Academic Press, 1973), pp. 48–267; and Barany and Merrifield in "The Peptides," eds. E. Gross and F. Meinenhofer, Vol. 2 (Academic Press, 1980), pp. 3–285. The synthesis is commenced from the carboxy-terminal end of the peptide using an alphaamino protected amino acid. Fluorenylmethyloxy-carbonyl (Fmoc) or t-butyloxycarbonyl (Boc) protective groups can be used for all amino groups even through other protective groups are suitable. For example, Boc-Asn-OH, Boc-Ser-OH, Boc-Phe-OH, Boc-Arg-OH or Boc-Tyr-OH (i.e., selected ANP analog carboxy-terminal amino acids) can be esterified to chloromethylated polystyrene resin supports. The polystyrene resin support is preferably a copolymer of styrene with about 0.5 to 2% divinyl benzene as a cross-linking agent which causes the polystyrene polymer to be insoluble in certain organic solvents. See Carpino et al., *J. Org. Chem.*, 37, 3404 (1972); Meinhofer, *Int. J. Pept. Pro. Res.*, 11, 246 (1978); and Merrifield, *J. Am. Chem. Soc.*, 85, 2149 (1963). These and other methods of peptide synthesis are also exemplified by U.S. Pat. Nos. 3,862,925; 3,842,067; 3,972,859, 4,105,602 and U.S. Pat. No. 4,757,048.

The immobilized peptide is then N-deprotected and other amino acids having protected amino groups are added in a stepwise manner to the immobilized peptide. At the end of the procedure, the final peptide is cleaved from the resin, and any remaining protecting groups are removed, by treatment under acidic conditions such as, for example, with a mixture of hydrobromic acid and trifluoroacetic acid or with hydrofluoric acid, or the cleavage from the resin may be effected under basic conditions, for example, with triethylamine, the protecting groups then being removed under acid conditions.

The cleaved peptides are isolated and purified by means well known in the art such as, for example, lyophilization followed by either exclusion or partition chromatography on polysaccharide gel media such as Sephadex G-25, or countercurrent distribution. The composition of the final peptide may be confirmed by amino acid analysis after degradation of the peptide by standard means.

Salts of carboxyl groups of the peptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

Acid addition salts of the polypeptides may be prepared by contacting the polypeptide with one or more equivalents of the desired inorganic or organic acid, such as, for example, hydrochloric acid.

Esters of carboxyl groups of the polypeptides may be prepared by any of the usual means known in the art for converting a carboxylic acid or precursor to an ester. One preferred method for preparing esters of the present polypeptides, when using the Merrifield synthesis technique described above, is to cleave the completed polypeptide from the resin in the presence of the desired alcohol either under basic or acidic conditions, depending upon the resin. Thus, the C-terminal end of the peptide when freed from the resin is directly esterified without isolation of the free acid.

Amides of the polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

The synthesis may use manual techniques or be completely automated, employing, for example, an Applied BioSystems 431A Peptide Synthesizer (Foster City, Calif.) or a Biosearch SAM II automatic peptide synthesizer (Biosearch, Inc., San Rafael, Calif.), following the instructions provided in the instruction manual and reagents supplied by the manufacturer. Disulfide bonds between Cys residues can be introduced by mild oxidation of the linear peptide by KCN as taught in U.S. Pat. No. 4,757,048 at Col. 20.

Alternatively, selected compounds of the present invention can be produced by expression of recombinant DNA constructs prepared in accordance with well-known methods such as those described in Seihamer et al. (U.S. Pat. No. 5,114,923), entitled "Recombinant Techniques for Production of Novel Natriuretic and Vasodilator Peptides." Such production can be desirable to provide large quantities or alternative embodiments of such compounds.

2. Structural Features

The compounds of the invention contain the pentapeptide core sequence $A_3$-$A_4$-$A_5$, which, in preferred embodiments, corresponds to the conserved region DRI present in ANP, CNP and BNP. Preferably, the sequence $A_1$—$A_2$—$A_3$—$A_4$—$A_5$ is RMDRI (SEQ ID NO: 10), KMDRI (SEQ ID NO: 11), KLDRI (SEQ ID NO: 12), KIDRI (SEQ ID NO: 18) or RLDRI (SEQ ID NO: 14), most preferably, is the KLDRI (SEQ ID NO: 12) sequence of rat, porcine or human CNP.

Preferably, $X_1$ is (H)GLSKG-(SEQ ID NO: 15) wherein (H) indicates the amino terminus of the peptide; and $X_4$ is —NSFRY(R) (SEQ ID NO: 16), wherein (R) is preferably (OH), indicating the carboxy terminus of the peptide. Preferably, $X_2$ is a tripeptide, most preferably -FGL-, or a dipeptide such as -FG- or -GL-, and $X_3$ is a heptapeptide, most preferably -GSMSGLG- (SEQ ID NO: 17). $X_3$ can also be a truncated form of -GSMSGLG- (SEQ ID NO: 17) wherein one or more of the Gly or Ser residues may be replaced by another of Gly (G), Ser (S) or Cys (C) or by Ala, and Leu may be replaced by Val or Ile.

The cyclic disulfides included within the invention are directly analogous to the naturally occurring CNPs, which contain 17 amino acid residue-membered disulfide rings, inclusive of the two cysteine residues which provide the sulfhydryl groups for the formation of the disulfide bond. However, those embodiments of the compounds of the invention which contain the cyclic disulfide may contain either more, or less, than 17 amino acid residues in the cyclic structure.

As indicated, the cyclic compounds of the present invention can be provided by bonding cysteine residues, or alternate amino acid residues $A_y$ and $A_z$ with an equivalent bond or linking group such as, for example, —$CH_2$—$CH_2$—. The replacement of a sulfhydryl group on the cysteine residue with an alternative group will effectively replace the cysteine residue with an alternative amino acid. For example, to replace one sulfhydryl group with a —$CH_2$— group, the cysteine residues will be replaced by the analogous alpha-aminobutyric acid. These cyclic analog peptides can be formed, for example, in accordance with the methodology of M. Lebl and V. J. Hruby, *Tetrahedron Lett.*, 25, 2067 (1984), or by employing the procedure disclosed in U.S. Pat. No. 4,161,521.

Ester or amide bridges may also be formed by reacting the OH or serine or threonine and the carboxyl of aspartic acid or glutamic acid, to yield a bridge of the structure —$CH_2$—$CO_2CH_2$—. Similarly, an amide can be obtained by reacting the side-chain of lysine and aspartic or glutamic acid to yield a bridge of the structure —$CH_2C(O)NH$—$(CH_2)_4$—. Methods for synthesis of these bridges are found in P. W. Schiller et al., *Biochem. Biophy. Res. Comm.*, 127 558 (1985); *Int. J. Peptide and Protein Res.*, 25, 171 (1985). Other bridge-forming amino acid residues and reactions are provided in U.S. Pat. No. 4,935,492.

The following references describe preparation of peptide analogs which include non-peptidyl bonds to link amino acid residues. A. F. Spatola, *Vega Data*, Vol. 1, Issue 3 (March 1983), "Peptide Backbone Modifications" (general review); A. F. Spatola in "Chemistry and Biochemistry of Amino Acids Peptides and Proteins", B. Weinstein, eds., Marcel Dekker, New York, p. 267 (1983) (general review); J. S. Morley, *Trends Pharm. Sci.* (1980) at pp. 463–468 (general review); D. Hudson et al., *Int. J. Pept. Prot. Res.*, 14, 177 (1979); (—$CH_2NH$—, —$CH_2C$—$H_2$—); A. F. Spatola et al., *Life Sci.*, 38, 1243 (1986) (—$CH_2$—S); M. M. Hann, *J. Chem. Soc. Perkin Trans. I*, 307 (1982) (—CH═CH—), cis and trans); R. G. Almquist et al., *J. Med. Chem.*, 23, 1392 (1980) (—$COCH_2$—); C. Jennings-White et al., *Tetrahedron Lett.*, 23, 2533 (1982) (—$COCH_2$—); M. Szelke et al., European Patent Appln EP 45665 (1982) (—C(OH)$CH_2$—); M. W. Holladay et al., *Tetrahedron Lett.*, 24, 4401 (1983) (—C(OH)$CH_2$—); and V. J. Hruby, *Life Sci.*, 31, 189 (1982) (—$CH_2$—S—).

3. Doses and Dosage Forms

The compounds of the present invention have natriuretic, diuretic and hypotensive activity in the intact mammal, and may possess vasorelaxant activity and/or inhibit the release of aldosterone and renin.

Thus, these compounds, and compositions containing them, can find use as therapeutic agents in the treatment of various edematous states such as, for example, congestive heart failure, nephrotic syndrome and hepatic cirrhosis, in addition to hypertension and renal failure due to ineffective renal perfusion or reduced glomerular filtration rate.

The present invention also provides compositions containing an effective amount of compounds of the present invention, including the nontoxic addition salts, amides and esters thereof, together with physiologically acceptable liquid, gel or solid diluents, adjuvants and excipients.

These compounds and compositions can be administered to mammals for veterinary use, such as with domestic animals, and for clinical use in humans in a manner similar to other therapeutic agents. In general, the dosage required for therapeutic efficacy will range from about 0.01 to 1000 mcg/kg, more usually 0.1 to 1000 mcg/kg of the host body weight. Dosages within these ranges can be administered via bolus doses, via a plurality of unit dosage forms, or by constant infusion over an extended period of time, usually exceeding 24 hours, until the desired therapeutic benefits have been obtained.

Typically, such compositions are prepared for injection or infusion, either as liquid solutions or suspensions. Solid forms suitable for solution in, or suspension in, liquid vehicles prior to injection or infusion may also be prepared. The preparation may also be emulsified. The active ingredient can be mixed with diluents or excipients which are physiologically acceptable and compatible with the active ingredient(s). Suitable diluents and excipients are, for example, water, saline, PBS, glycerol, or the like, and combinations thereof. In addition, if desired, the compositions may contain minor amounts of auxiliary substances such as wetting or emulsifying agents, stabilizing or pH-buffering agents, and the like.

Such compositions are conventionally administered parenterally, by injection, for example, either subcutaneously or intravenously. Formulations which are suitable for other modes of administration include suppositories, insufflated powders or solutions, eyedrops, nosedrops, intranasal aerosols, and, in some cases, oral formulations. Oral formulations include such normally employed excipients as, for example, pharmaceutical grades of alkylcelluloses, mannitol, dextrose, lactose, starch, magnesium stearate, sodium saccharin, cellulose, magnesium carbonate, and the like. Thus, these compositions can take the form of solutions, suspensions, tablets, pills, hard or soft gelatin capsules, sustained-release formulations such as liposomes, gels or hydrogels; or powders, and can contain 10%–95% of active ingredient, preferably 25%–70%.

The peptide compounds may be formulated into the compositions as neutral or salt forms. Pharmaceutically acceptable nontoxic salts include the acid addition salts (formed with the free amino groups) and which are formed by reaction with inorganic acids such as, for example, hydrochloric, sulfuric or phosphoric acids, or organic acids such as, for example, acetic, oxalic, tartaric, mandelic, citric, malic, and the like. Salts formed with the free carboxyl groups may be derived from inorganic bases such as, for example, sodium, potassium, ammonium, calcium, or ferric hydroxides, and such organic bases such as amines, i.e., isopropylamine, trimethylamine, 2-ethylamino ethanol, histidine, procaine, and the like.

4. Other Utility

In addition to the compounds of the present invention which display natriuretic, diuretic or vasorelaxant activity, compounds of the present invention can also be employed as intermediates in the synthesis of such useful compounds. Alternatively, by appropriate selection, compounds of the present invention whose activity levels are reduced or eliminated entirely can serve to modulate the activity of other diuretic, natriuretic or vasorelaxant compounds, including compounds outside the scope of the present invention by, for example, binding to alternate receptors, stimulating receptor turnover, or providing alternate substrates for degradative enzyme or receptor activity and thus inhibiting these enzymes or receptors. When employed in this manner as antagonists, such compounds can be delivered as admixtures with other active compounds or can be delivered separately, for example, in their own carriers.

Compounds of the present invention can also be used to prepare antisera for use in immunoassays employing labeled reagents, usually antibodies. Conveniently, the peptides can be conjugated to an antigenicity-conferring carrier, if necessary, by means of dialdehydes, carbodiimide or by using commercially available linkers. These compounds and immunologic reagents may be labeled with a variety of labels such as chromophores, fluorophores such as, e.g., fluorescein or rhodamine, radioisotopes such as $^{125}I$, $^{35}S$, $^{14}C$, or $^{3}H$, or magnetized particles, by means known to the art.

These labeled compounds and reagents, or labeled reagents capable of recognizing and specifically binding to them, can find use as, e.g., diagnostic reagents. Samples derived from biological specimens can be assayed for the presence or amount of substances having a common antigenic determinant with compounds of the present invention. In addition, monoclonal antibodies can be prepared by methods known in the art, which antibodies can find therapeutic use, e.g., to neutralize overproduction of immunologically related compounds in vivo.

The invention will be further described by reference to the following detailed examples wherein VNP was synthesized in the Mayo Protein Core Facility using fluorenylmethoxycarbonyl (FMOC) chemistry on an ABI 431A peptide synthesizer (Applied Biosystems Inc., Foster City, Calif.) with the protocols and reagents supplied by the manufacturer. The peptide was purified by reverse phase high performance liquid chromatography (HPLC) using a Vydac C8 column (The Separations Group, Hesperia, Calif.). The synthesis was confirmed by amino acid analysis and plasma absorption mass spectrometry.

The samples from the plasma and urine were analyzed using reverse phase HPLC with a Vydac C18 column (4.6 mm×250 mm) (The Separations Groups, Hesperia, Calif.). The components of the HPLC system were two Beckman 114 pumps (Beckman Instruments, San Ramon, Calif.), ABI 759A absorbance detector (Applied Biosystems, Inc., Foster City, Calif.), and an IBM PS2 50Z computer with Beckman System Gold Chromatography software. The A buffer was 0.1% trifluoracetic acid and the B buffer was 80% acetonitrile/20% water/0.1% trifluoroacetic acid. The separation was performed with a gradient of 5% to 70% B buffer in 60 minutes.

The results obtained are expressed as the means ±SEM. In organ chamber studies, n equals the number of dogs from which rings were taken. Rings with and without endothelium were studied in parallel, and Student's t-test for unpaired observations was used to determine statistical significance among the responses of rings with and without endothelium and between responses of arteries and veins. In rat studies, the data were analyzed using ANOVA for repeated measures followed by Fisher's least significant difference test when appropriate within the group. Data between groups were analyzed by Student's unpaired t-test. Statistical significance was determined at p<0.05.

Example 1. In Vitro Studies

Rings cut from femoral, saphenous, renal and pulmonary arteries and veins obtained from random source mongrel dogs (anesthetized with 30 mg/kg pentobarbital sodium intravenously) were suspended for the measurement of isometric force in organ chambers filled with aerated (95% $O_2$ and 5% $CO_2$) modified Krebs-Ringer bicarbonate solution (composition in mM: 118.3 NaCl, 4.7 KCl, 2.5 $CaCl_2$, 1.2 $MgSO_4$, 1.2 $KH_2PO_4$, 25.0 $NaHCO_3$, 0.026 calcium sodium EDTA, and 11.1 dextrose; control solution) at 37° C. In one-half rings, the endothelium was removed by gently rubbing the intimal surface with a cotton swab wetted with control solution. Each ring was stretched to the optimal point on its length-tension curve as determined by the tension developed to norepinephrine ($3 \times 10^{-7}$M) at each level of stretch. The presence of endothelium was determined at the beginning of the experiment by a relaxation to acetylcholine ($10^{-6}$M) during a contraction to norepinephrine at optimal length. The maximal tension of each ring was determined by norepinephrine ($10^{-4}$M). To study responses to ANP, CNP and VNP, the rings were contracted with phenylephrine ($10^{-6}$M). These contractions averaged 30–40% of the maximal contraction to norepinephrine. The peptides were added cumulatively once the contraction had stabilized.

The following commercially available drugs were used: acetylcholine chloride (Sigma Chemical, St. Louis, Mo.), human ANP and human CNP (Peninsula Laboratories, Belmont, Calif.), L-norepinephrine bitartrate (Sigma), phenylephrine bitartrate (Sigma). All drugs were dissolved in distilled water immediately prior to study, and the concentrations are reported as the final molar concentration (M) in the organ chamber.

At maximal dose ($3 \times 10^{-6}$ log M), ANP and CNP had no effects on femoral and saphenous arteries and veins, but VNP exposure resulted in a potent relaxation (90–100%) in femoral and saphenous arteries. In femoral and saphenous veins, ANP had no effect. CNP relaxes femoral veins by 90% and saphenous veins by 40%. VNP caused a 90% relaxation in both femoral and saphenous veins.

Table 1 summarizes the maximal relaxations ($3 \times 10^{-6}$M) of ANP, CNP and VNP in isolated normal canine blood vessels.

TABLE 1

The maximal responses of ANP, CNP and VNP ($3 \times 10^{-6}$M) in isolated normal canine blood vessels.

| | | ANP (n = 6–9) | CNP (n = 6–9) | VNP (n = 4–6) |
|---|---|---|---|---|
| Systemic blood vessels | | | | |
| Arteries | Endothelium | | | |
| Femoral | with | 10 ± 5§ | 4 ± 3 | 91 ± 4*+ |
| | without | 19 ± 12 | 10 ± 6 | 89 ± 5*+ |
| Saphenous | with | 0 ± 0 | 11 ± 7 | 73 ± 3*+ |
| | without | 3 ± 3 | 14 ± 8 | 81 ± 5*+ |
| Renal | with | 27 ± 6+ | 8 ± 2 | 52 ± 4*+ |
| | without | 30 ± 6+ | 8 ± 2 | 62 ± 12*+ |

TABLE 1-continued

The maximal responses of ANP, CNP and VNP ($3 \times 10^{-6}$M) in isolated normal canine blood vessels.

| | | ANP (n = 6–9) | CNP (n = 6–9) | VNP (n = 4–6) |
|---|---|---|---|---|
| Veins | | | | |
| Femoral | with | 6 ± 3 | 37 ± 8* | 81 ± 6*+ |
| | without | 4 ± 4 | 73 ± 8*¶ | 86 ± 6* |
| Saphenous | with | 0 ± 0 | 16 ± 1* | 60 ± 11*+ |
| | without | 0 ± 0 | 43 ± 10* | 89 ± 6*+ |
| Renal | with | 12 ± 3 | 43 ± 4* | 65 ± 6*+ |
| | without | 11 ± 4 | 71 ± 5*¶ | 90 ± 4*+¶ |
| Pulmonary blood vessels | | | | |
| Artery | with | 60 ± 7+ | 12 ± 3 | 57 ± 5+ |
| | without | 75 ± 8+¶ | 33 ± 5¶ | 63 ± 7+ |
| Vein | with | 49 ± 5 | 31 ± 6* | 71 ± 2*+ |
| | without | 16 ± 3¶ | 66 ± 4*¶ | 84 ± 3*+¶ |

§ Data are shown as Mean ± SEM of a percent change in tension from a contraction to phenylephrine ($10^{-6}$M).
*p < .05 vs ANP
+ p < .05 vs CNP
¶ p < .05 vs with endothelium
ANP atrial natriuretic peptide
CNP C-type natriuretic peptide
VNP vasonatrin peptide In systemic arteries (femoral, saphenous and renal), ANP and CNP produced modest relaxations with the maximum being less than 30% of the contraction to phenylephrine. VNP, on the other hand, produced relaxations which ranged between 50–90% of the contraction; these relaxations were not modified significantly by the endothelium. In the comparable systemic veins, relaxations to CNP were significantly greater than relaxations evoked by ANP. Relaxations to CNP were increased significantly by removal of the endothelium. Relaxations induced by VNP were significantly greater than those induced by CNP in all systemic veins tested. Only in the renal veins were the relaxations enhanced by removal of the endothelium. The potency for relaxation in the systemic blood vessels for the peptides can be summarized as: VNP>ANP≧CNP in arteries; VNP>CNP>ANP in veins.

In the pulmonary blood vessels, all three peptides produced significant relaxation. The order of potency in pulmonary arteries is: ANP=VNP>CNP. Relaxations induced by ANP and CNP were increased by removal of the endothelium. The order of potency in the pulmonary veins without endothelium is: VNP>CNP>ANP. Relaxations induced by ANP were greater in the presence of endothelium while those to CNP and VNP were greater in the absence of the endothelium.

Example 2. In Vivo Studies

Experiments were conducted in accordance with the Animal Welfare Act. Wistar rats and spontaneously hypertensive rats (SHR) (400 g; Harlan Sprague-Dawley, Indianapolis, Ind.) were anesthetized with Inactin (100 mg/kg; intraperitoneal; BYK Gulden, Konstanz, Germany). The body temperature was maintained between 36° and 38° C. by a heating pad. Tracheostomy was performed; however, the animals were not artificially ventilated. Polyethylene catheters (PE-50; Becton Dickinson Co., Parsippany, N.J.) were placed in the left jugular vein for infusions of saline and drugs, in the right jugular vein to right atrium to monitor right atrial pressure, and in the carotid artery for the collection of blood samples and to monitor mean arterial pressure.

A PE-90 catheter was placed in the bladder for urine collection.

Experiments were conducted in three groups in normal rats: ANP group (n=4), CNP group (n=4), and VNP group (n=4). VNP also was studied in SHR rats (n=4). Intravenous infusions of saline solution (0.9% NaCl) were performed (1 ml/100 gm body weight/hr) through the left jugular vein catheter. After completion of surgery, rats were allowed to stabilize for 30 minutes. In each group, a 15-min baseline period followed. After the baseline period, saline solution (0.9% NaCl) was administered in a bolus fashion (0.1 ml) and was followed by a 15-min period. After the saline period, the peptide (ANP, CNP or VNP) was administered in a bolus fashion (0.1 ml) at 5 µg/kg which was followed by a 15-min period. This was followed by a second bolus (0.1 ml) at 50 µg/kg and a 15-min period. After a 30-min washout, a 15-min recovery period followed. During each experimental period, mean arterial pressure (MAP), heart rate (HR), and right atrial pressure (RAP) were measured. At the midpoint of baseline, second bolus fashion (50 µg/kg) and recovery periods, blood was sampled for plasma cGMP.

At the end of each period, urine was measured for volume (UV), and samples were stored for electrolytes and cGMP analysis.

Blood for plasma cGMP analysis was collected into EDTA tubes, immediately placed on ice, and centrifuged at 2,5000 rpm at 4° C. Plasma was separated and stored at −20° C. until assay. Urine for cGMP determination was heated to >90° C. before storage. Plasma and urine cGMP were determined by a specific RIA as previously described by A. L. Steiner et al., *J. Hypertension*, 5 (Suppl. 5) 551–553 (1987).

Table 2 summarizes the cardiovascular and renal actions of ANP, CNP and VNP administration in normal rats.

TABLE 2

| | | Baseline | Saline | 5 µg/kg | 50 µg/kg | Recovery |
|---|---|---|---|---|---|---|
| ANP group (n = 4) | | | | | | |
| MAP | (mmHg) | 119 ± 14 | 120 ± 14 | 97 ± 12* | 69 ± 7*+ | 92 ± 11*¶ |
| HR | (beats/min) | 375 ± 23 | 365 ± 17 | 353 ± 14 | 355 ± 19 | 368 ± 23 |
| RAP | (mmHg) | 0.8 ± 1.6 | 0.5 ± 1.8 | −2.3 ± 0.8* | −3.8 ± 0.8*+ | −0.8 ± 0.9¶ |
| UV | (µl/min) | 6.7 ± 1.2 | 7.2 ± 1.8 | 79 ± 10* | 341 ± 41*+ | 48 ± 14¶ |
| UNaV | (µmol/min) | 0.4 ± 0.1 | 0.4 ± 0.1 | 13.2 ± 3.5* | 68.2 ± 15.7*+ | 8.9 ± 3.5¶ |
| UKV | (µmol/min) | 1.8 ± 0.1 | 0.7 ± 0.1 | 10.3 ± 3.5 | 24.4 ± 8.7 | 2.4 ± 0.1 |
| PcGMP | (pmol/ml) | 4.1 ± 0.7 | 12 ± 2 | — | 25.7 ± 7.1* | 3.2 ± 0.3¶ |
| UcGMPV | (pmol/min) | 11 ± 2 | 12 ± 2 | 605 ± 151* | 2580 ± 505*+ | 105 ± 63¶ |
| CNP group (n = 4) | | | | | | |
| MAP | (mmHg) | 116 ± 11 | 115 ± 12 | 100 ± 12* | 87 ± 9*+ | 104 ± 11*¶ |
| HR | (beats/min) | 350 ± 9 | 360 ± 14 | 363 ± 19 | 365 ± 19 | 363 ± 16 |
| RAP | (mmHg) | 1.2 ± 0.9 | 0.2 ± 1.4 | 0 ± 1.5 | −2.3 ± 0.6* | −0.1 ± 0.9* |
| UV | (µl/min) | 5.7 ± 0.5 | 5.7 ± 0.6 | 27.6 ± 2.0*§ | 66.4 ± 7.4*+§ | 21.2 ± 6.3¶ |
| UNaV | (µmol/min) | 0.6 ± 0.2 | 0.6 ± 0.2 | 4.1 ± 1.4§ | 12.1 ± 3.2*+§ | 2.9 ± 0.3 |
| UKV | (µmol/min) | 1.2 ± 0.3 | 1.2 ± 0.3 | 5.1 ± 1.6 | 7.6 ± 2.5 | 2.4 ± 1.1 |
| PcGMP | (pmol/ml) | 2.2 ± 0.1 | — | — | 19.4 ± 2.7* | 3.6 ± 0.3¶ |
| UcGMPV | (pmol/min) | 23 ± 7 | 22 ± 6 | 97 ± 32§ | 323 ± 81*§ | 70 ± 39¶ |
| VNP group (n = 4) | | | | | | |
| MAP | (mmHg) | 112 ± 14 | 109 ± 12 | 93 ± 15* | 79 ± 15*+ | 93 ± 15*¶ |
| HR | (beats/min) | 390 ± 24 | 398 ± 22 | 393 ± 20 | 408 ± 25 | 390 ± 20 |
| RAP | (mmHg) | −2.5 ± 0.6 | −2.1 ± 0.7 | −3.5 ± 0.9 | −4.3 ± 0.8* | −2.9 ± 0.9¶ |
| UV | (µl/min) | 6.5 ± 1.1 | 6.4 ± 0.3 | 32.2 ± 7.5*§ | 136 ± 5.5*+§# | 8.4 ± 2.7¶ |
| UNaV | (µmol/min) | 0.9 ± 0.3 | 0.7 ± 0.2 | 5.3 ± 1.9 | 22.5 ± 2.2*+§# | 0.9 ± 0.3¶ |
| UKV | (µmol/min) | 0.9 ± 0.1 | 1.0 ± 0.2 | 3.3 ± 1.4 | 11.9 ± 4.7 | 1.3 ± 0.6 |
| PcGMP | (pmol/ml) | 3.7 ± 1.2 | — | — | 33.3 ± 8.7* | 4.4 ± 1.4¶ |
| UcGMPV | (pmol/ml) | 13 ± 7 | 12 ± 6 | 113 ± 27*§ | 961 ± 82*+§# | 88 ± 48¶ |

Mean ± SEM
*p < .05 vs Baseline
+ p < .05 vs 5 µg/kg
¶ p < .05 vs 50 µg/kg
§ p < .05 vs ANP group
# p < .05 vs CNP group
ANP atrial natriuretic peptide
CNP C-type natriuretic peptide
VNP vasonatrin peptide
MAP mean arterial pressure
HR heart rate
RAP right atrial pressure
UV urine volume
UNaV urine sodium excretion
UKV urine potassium excretion
PcGMP plasma cGMP
UcGMPV urine cGMP volume As demonstrated by the data in Table 2, bolus administration (0.1 ml) of saline solution had no cardio-vascular or renal actions. Bolus administration (0.1 ml) of high dose (50 µg/kg) ANP, CNP and VNP resulted in a significant decrease in MAP and RAP, and increased urine flow, sodium excretion, plasma cGMP and urinary cGMP volume. The increase in urine flow, sodium excretion and urinary cGMP volume were significantly higher with VNP than those of CNP, but were less than those of ANP.

Table 3 reports the cardiovascular and renal effects of VNP in normal and SHR rats.

TABLE 3

The cardiorenal actions of VNP in normal and SHR rats

|  |  | Baseline | Saline | 5 µg/kg | 50 µg/kg | Recovery |
|---|---|---|---|---|---|---|
| Normal rats (n = 4) | | | | | | |
| MAP | (mmHg) | 112 ± 14 | 109 ± 12 | 93 ± 15* | 79 ± 15*+ | 93 ± 15*¶ |
| HR | (beats/min) | 390 ± 24 | 398 ± 22 | 393 ± 20 | 408 ± 25 | 390 ± 20 |
| RAP | (mmHg) | −2.5 ± 0.6 | −2.1 ± 0.7 | −3.5 ± 0.9 | −4.3 ± 0.8* | −2.9 ± 0.9¶ |
| UV | (µl/min) | 6.5 ± 1.1 | 6.4 ± 0.3 | 32.2 ± 7.5* | 136 ± 5.5*+ | 8.4 ± 2.7¶ |
| UNaV | (µmol/min) | 0.9 ± 0.3 | 0.7 ± 0.2 | 5.3 ± 1.9 | 22.5 ± 2.2*+ | 0.9 ± 0.3¶ |
| UKV | (µmol/min) | 0.9 ± 0.1 | 1.0 ± 0.2 | 3.3 ± 1.4 | 11.9 ± 4.7 | 1.3 ± 0.6 |
| PcGMP | (pmol/ml) | 3.7 ± 1.2 | — | — | 33.3 ± 8.7* | 4.4 ± 1.4¶ |
| UcGMPV | (pmol/min) | 13 ± 7 | 12 ± 6 | 113 ± 27* | 961 ± 82*+ | 88 ± 48¶ |
| SHR rats (n = 4) | | | | | | |
| MAP | (mmHg) | 169 ± 17§ | 168 ± 17§ | 132 ± 23* | 119 ± 20*+ | 138 ± 19*¶ |
| HR | (beats/min) | 388 ± 13 | 390 ± 11 | 393 ± 13 | 405 ± 10 | 405 ± 17 |
| RAP | (mmHG) | 0.5 ± 1.2 | 0.5 ± 1.3 | −1.1 ± 0.8 | −2.5 ± 0.6*+ | −0.9 ± 1.0¶ |
| UV | (µl/min) | 3.7 ± 0.3§ | 3.8 ± 0.7§ | 26.8 ± 3.5* | 48.2 ± 7.4*+§ | 9.1 ± 3.7¶ |
| UNaV | (µmol/min) | 0.5 ± 0.2 | 0.6 ± 0.2 | 5.2 ± 1.6* | 9.2 ± 2.1*+§ | 1.7 ± 0.7¶ |
| UKV | (µmol/min) | 0.6 ± 0.2 | 0.6 ± 0.2 | 3.9 ± 1.5 | 6.6 ± 2.6 | 1.1 ± 0.4 |
| PcGMP | (pmol/ml) | 3.1 ± 0.7 | — | — | 17.7 ± 3.6* | 3.1 ± 0.5¶ |
| UcGMPV | (pmol/min) | 9 ± 1 | 8 ± 2 | 115 ± 27* | 234 ± 42*+§ | 26 ± 12¶ |

Mean ± SEM
*$p < .05$ vs Baseline
+ $p < .05$ vs 5 µg/kg
¶ $p < .05$ vs 50 µg/kg
§ $p < .05$ vs normal rats
SHR spontaneous hypertensive rat
VNP vasonatrin peptide
MAP mean arterial pressure
HR heart rate
RAP right arterial pressure
UV urine volume
UNaV urine sodium excretion
UKV urine potassium excretion
PcGMP plasma cGMP
UcGMPV urine cGMP volume As shown by the data in Table 3, the baseline MAP of SHR was significantly higher than that of normal rats, and the baseline urine volume of SHR was markedly lower than that of normal rats. During high dose bolus infusion of VNP, MAP and RAP significantly decreased, urine flow, sodium excretion, plasma cGMP and urinary cGMP volume were significantly increased in both normal and SHR groups. While the lowering of MAP to VNP was similar in both groups, the renal actions and urinary cGMP effects of VNP were attenuated in SHR rats as compared to normal rats. VNP is a more potent, endothelium independent vasorelaxing peptide in both arteries and veins as compared to ANP and CNP. VNP also has a potent natriuretic effect in vivo.

Examples 1 and 2 confirm that ANP is a potent natriuretic and vasoactive peptide, which has vasorelaxing actions in renal and pulmonary arteries. As shown by K. J. Koller et al., Science, 251, 120 (1991), these biological actions of ANP are mediated through the ANPR-A receptor. CNP has potent vasodilator actions in veins with less actions in arteries, while not exhibiting natriuretic effects. See C. M. Wei et al., Am. J. Physiol., 264, H71 (1993); A. J. Stingo et al., Am. J. Physiol., 262, H308 (1992). The biological actions of CNP are mediated through ANPR-B receptor. (See K. J. Koller, cited above.) In the present study, CNP was also confirmed to exhibit hemodynamic actions similar to those previously reported. However, CNP in the rat, unlike the dog, has modest but significant natriuretic actions.

The structural difference between ANP and CNP is a difference in amino acid sequences and CNP lacks a COOH-terminus. Thus, preferred peptides of the invention share properties of both ANP and CNP, suggesting that COOH-terminus may play an important role for biological activity, possibly by leading to binding to both the ANPR-A and ANPR-B receptors. Furthermore, in femoral vein and pulmonary artery, CNP has more potent effects in vessels without endothelium, but the actions of VNP are similar with and without the presence of endothelium. This may be due to endothelial mechanism(s) which inhibit the actions of CNP but not VNP. This may also be related to the presence of the VNP COOH-terminus.

Because VNP has potent arterial and venous vasodilating actions and natriuretic effects, the peptides of the invention may be useful in the treatment of cardiovascular and renal diseases, such as hypertension, congestive heart failure, and eclampsia. In preliminary studies, VNP also exhibits potent vasorelaxing actions in isolated vessels in congestive heart failure dogs. Moreover, this peptide is also able to relax vessels pre-contracted with endothelin, which is a potent endothelium-derived vasoconstrictor.

All publications and patents cited herein are herein incorporated by reference to the same extent as if each individual publication or patent was specifically and individually indicated to be incorporated by reference.

It will be apparent to one of ordinary skill in the art that many changes and modifications can be made in the invention without departing from the spirit or scope of the appended claims.

What is claimed is:

1. A peptide compound of the formula:

(H)-Gly-Leu-Ser-Lys-Gly-Cys-Phe-Gly-Leu-Lys-Leu-Asp-

Arg-Ile-Gly-Ser-Met-Ser-Gly-Leu-Gly-Cys-Asn-Ser-Phe-

Arg-Tyr-(R)

(SEQ ID NO: 4), wherein R is OH, $NH_2$, $NHR^3$ or $N(R^3)(R^4)$, wherein $R^3$ and $R^4$ are independently phenyl or $(C_1-C_4)$alkyl; wherein the bracket connecting the two Cys residues indicates that they are connected by a disulfide bond; or a pharmaceutically acceptable salt thereof.

2. A composition useful as a natriuretic, diuretic or vasodilator comprising a therapeutically effective amount of the compound of claim 1, in combination with a pharmaceutically acceptable carrier.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 28 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: Mature human atrial natriuretic peptide
(ANP)

( x i ) SEQUENCE DESCRIPTION: SEQ ID NO:1:

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

( 2 ) INFORMATION FOR SEQ ID NO:2:

( i ) SEQUENCE CHARACTERISTICS:
( A ) LENGTH: 32 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: Mature human brain natriuretic peptide
(BNP)

( x i ) SEQUENCE DESCRIPTION: SEQ ID NO:2:

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

( 2 ) INFORMATION FOR SEQ ID NO:3:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: Mature human C-type natriuretic peptide
(CNP)

( x i ) SEQUENCE DESCRIPTION: SEQ ID NO:3:

Gly Leu Ser Lys Gly Cys Phe Gly Leu Lys Leu Asp Arg Ile Gly Ser
1               5                   10                  15

Met Ser Gly Leu Gly Cys
            20

( 2 ) INFORMATION FOR SEQ ID NO:4:

( i ) SEQUENCE CHARACTERISTICS:
    ( A ) LENGTH: 27 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: Vasonatrin peptide (VNP)

( x i ) SEQUENCE DESCRIPTION: SEQ ID NO:4:

```
Gly Leu Ser Lys Gly Cys Phe Gly Leu Lys Leu Asp Arg Ile Gly Ser
1               5                   10                  15
Met Ser Gly Leu Gly Cys Asn Ser Phe Arg Tyr
            20                  25
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear     ( i i ) MOLECULE TYPE: peptide     ( v i ) ORIGINAL SOURCE:
        ( A ) ORGANISM: Fragment of X1 of Formula I     ( x i ) SEQUENCE DESCRIPTION: SEQ ID NO:5:

```
Gly Leu Ser Lys Gly
1               5
```

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear     ( i i ) MOLECULE TYPE: peptide     ( v i ) ORIGINAL SOURCE:
        ( A ) ORGANISM: Fragment of X1 of Formula I     ( x i ) SEQUENCE DESCRIPTION: SEQ ID NO:6:

```
Leu Ser Lys Gly
1
```

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear     ( i i ) MOLECULE TYPE: peptide     ( v i ) ORIGINAL SOURCE:
        ( A ) ORGANISM: Amino acid residue of Xy of Formula I     ( x i ) SEQUENCE DESCRIPTION: SEQ ID NO:7:

```
Arg Phe Ser Asn
1
```

( 2 ) INFORMATION FOR SEQ ID NO:8:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Amino acid residue of Xy of Formula I (xi) SEQUENCE DESCRIPTION: SEQ ID NO:8:

Tyr Arg Phe Ser Asn
1               5

(2) INFORMATION FOR SEQ ID NO:9:

(i) SEQUENCE CHARACTERISTICS:
    (A) LENGTH: 22 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Formula II (xi) SEQUENCE DESCRIPTION: SEQ ID NO:9:

Gly Leu Ser Lys Gly Cys Phe Gly Leu Xaa Xaa Asp Arg Ile Gly Ser
1               5                   10                  15

Met Ser Gly Leu Gly Cys
            20

(2) INFORMATION FOR SEQ ID NO:10:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:10:

Arg Met Asp Arg Ile
1               5

(2) INFORMATION FOR SEQ ID NO:11:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:11:

Lys Met Asp Arg Ile
1               5

(2) INFORMATION FOR SEQ ID NO:12:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide ( x i ) SEQUENCE DESCRIPTION: SEQ ID NO:12:

Lys Leu Asp Arg Ile
1               5

( 2 ) INFORMATION FOR SEQ ID NO:13:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:13:

Lys Ile Asp Arg Ile
1               5

( 2 ) INFORMATION FOR SEQ ID NO:14:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

Arg Leu Asp Arg Ile
1               5

( 2 ) INFORMATION FOR SEQ ID NO:15:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

Gly Leu Ser Lys Gly
1               5

( 2 ) INFORMATION FOR SEQ ID NO:16:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:16:

Asn Ser Phe Arg Tyr
1               5

( 2 ) INFORMATION FOR SEQ ID NO:17:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide (xi) SEQUENCE DESCRIPTION: SEQ ID NO:17:

Gly Ser Met Ser Gly Leu Cys
1               5